(12) United States Patent
Buddhiraju et al.

(10) Patent No.: US 12,050,448 B2
(45) Date of Patent: Jul. 30, 2024

(54) METHOD AND SYSTEM TO CONTROL A CONTINUOUS BIOPROCESSING

(71) Applicant: Tata Consultancy Services Limited, Mumbai (IN)

(72) Inventors: Venkata Sudheendra Buddhiraju, Pune (IN); Venkataramana Runkana, Pune (IN); Vishnu Swaroopji Masampally, Pune (IN); Anshul Agarwal, Noida (IN); Amey Ahsok Kulkarni, Pune (IN); Keshari Nandan Gupta, Noida (IN); Navnath Manohar Deore, Pune (IN); Vinesh Balakrishnan Yezhuvath, Noida (IN); Anamika Tiwari, South Delhi (IN); Anurag Singh Rathore, South Delhi (IN); Garima Thakur, South Delhi (IN); Nikita Saxena, South Delhi (IN); Shantanu Banerjee, South Delhi (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 183 days.

(21) Appl. No.: 17/586,995

(22) Filed: Jan. 28, 2022

(65) Prior Publication Data
US 2022/0283561 A1    Sep. 8, 2022

(30) Foreign Application Priority Data

Jan. 29, 2021   (IN) ............................. 202121004083

(51) Int. Cl.
*G05B 19/05*    (2006.01)
*C12M 1/36*     (2006.01)
(Continued)

(52) U.S. Cl.
CPC ......... *G05B 19/054* (2013.01); *G05B 19/056* (2013.01); *G06N 5/01* (2023.01);
(Continued)

(58) Field of Classification Search
CPC ........................... G06F 11/0796; G06Q 50/163
See application file for complete search history.

(56) References Cited

U.S. PATENT DOCUMENTS 9,133,433 B2     9/2015  Vogel et al.
2012/0063039 A1*  3/2012  Shah .................. G06F 11/0793
                                                361/20
(Continued)

FOREIGN PATENT DOCUMENTS

CN        104395341 B    6/2018
KR    10-2013-0131352 A  12/2013
(Continued)

*Primary Examiner* — Getente A Yimer
(74) *Attorney, Agent, or Firm* — FINNEGAN, HENDERSON, FARABOW, GARRETT & DUNNER, LLP

(57) ABSTRACT

Process control of continuous production of biomolecules is a major challenge due to complex nature of processes and time scales of operations involved. Availability of key process variables in real-time is one of main requirements. This disclosure relates to a processor implemented method of controlling a continuous bioprocessing plant which includes at least one of: receiving, an input data associated with one or more equipments; generating, by a recipe builder, a sequence of unit operations to determine at least one job order based on the at least input data; obtaining, a control decision associated with a control parameter based on the at least one job order; communicating, via the middleware, the control decision associated with the control parameter to the PLC; and executing, by a control system of the PLC, the control decision on a unit equipment to control:

(Continued)

(i) a continuous bioprocessing train, and (ii) an individual unit operation.

13 Claims, 7 Drawing Sheets

(51) Int. Cl.
*G05B 13/04* (2006.01)
*G06N 5/01* (2023.01)
(52) U.S. Cl.
CPC .............. *G05B 2219/13149* (2013.01); *G05B 2219/14058* (2013.01); *G05B 2219/14083* (2013.01)

(56) References Cited

U.S. PATENT DOCUMENTS

| | | | |
|---|---|---|---|
| 2013/0217979 A1* | 8/2013 | Blackadar | A61B 5/1123 600/301 |
| 2014/0095114 A1* | 4/2014 | Thomeer | G06Q 10/20 702/187 |
| 2020/0042375 A1* | 2/2020 | Hobbs | G06F 11/0796 |
| 2020/0101399 A1 | 4/2020 | Skudas | |
| 2022/0019207 A1* | 1/2022 | Ramachandran | G06Q 50/163 |

FOREIGN PATENT DOCUMENTS

| | | |
|---|---|---|
| KR | 10-2014-0141562 A | 12/2014 |
| KR | 10-2021-0127947 A | 10/2021 |

* cited by examiner

METHOD AND SYSTEM TO CONTROL A CONTINUOUS BIOPROCESSING

PRIORITY CLAIM

This U.S. patent application claims priority under 35 U.S.C. § 119 to: India Application No. 202121004083, filed on Jan. 29, 2021. The entire contents of the aforementioned application are incorporated herein by reference.

TECHNICAL FIELD

This disclosure relates generally to control systems, and, more particularly, to method and system to control a continuous bioprocessing.

BACKGROUND

Typically, a production plant includes automated regulation and control of the units through a control system, especially a process control system (PCS). In the current scenario, the control system is connected to a control and observation station as an interface via which a user can control and observe the process. Advanced real time control strategies are critical for developing a robust continuous manufacturing process and running at a steady state and to enable integration of unit operations with different purposes, schedules, and flow rates. The problem with a batch manufacturing process is that it takes longer time to extract a required product from its prepared solution. Plug-and-play biopharmaceutical processes in which all parameters are rigidly fixed, and completely automated equipment that can run without supervision are difficult to achieve and may also lead to problems in quality of product. Most of the controls are not automated or manual in nature and require human intervention to perform a required control action. On the other hand, although continuous manufacturing is well established in multiple domains, it is not yet achieved completely in a biomanufacturing process. Complex automation requirements, design and sensing challenges, stringent regulatory requirements, business risks are some of the hurdles. Data acquisition has always been a challenging task in bioprocessing systems due to the complex nature of the process itself. There are various unit operations in the process where obtaining real-time measurements is quite challenging.

SUMMARY

Embodiments of the present disclosure present technological improvements as solutions to one or more of the above-mentioned technical problems recognized by the inventors in conventional systems. For example, in one aspect, a processor implemented method of controlling a continuous bioprocessing is provided. The processor implemented method includes at least one of: receiving, via one or more hardware processors, at least input data associated with one or more equipments through a data historian; generating, by a recipe builder, a sequence of unit operations to determine at least one job order based on the at least input data associated with the one or more equipments for the at least one unit operation; obtaining, via the one or more hardware processors, at least one control decision associated with at least one control parameter based on the at least one job order; communicating, via the middleware, the at least one control decision associated with at least one control parameter to the PLC in a PLC readable format; and executing, by a control system of the PLC, the at least one control decision on a unit equipment to control: (i) a continuous bioprocessing train by the PLC, and (ii) an individual unit operation. The at least input data corresponds to one or more process variables associated with the one or more equipments and a data associated with at least one unit operation. The one or more process variables corresponds to (i) a pressure, (ii) a turbidity, (iii) a concentration, (iv) a conductivity, (v) a pH, (vi) a temperature, and (vii) a flow rate. The at least one job order is transferred to a programmable logic controller (PLC) for execution via a middleware. The at least one control decision is obtained based on at least one of: (i) a model based control, or (ii) a recipe based control, or (iii) at least one pre-defined control parameters in the PLC, or (iv) a combination thereof.

In an embodiment, the one or more equipments corresponds to: (i) a bioreactor, (ii) an acoustic wave separator (AWS), (iii) a near infra-red (NIR) spectroscopy, (iv) a high-performance liquid chromatography (HPLC), (v) continuous capture chromatography, (vi) viral inactivation unit, (vii) continuous polishing chromatography, (viii) pumps, (ix) ultrafiltration-diafiltration unit, (x) in-line turbidity sensors, (xi) conductivity sensors, and (xii) a soft sensor. In an embodiment, the soft sensor corresponds to at least one of: (a) a physics-based model, (b) a data-based model, and (c) a hybrid physics plus data-based model. In an embodiment, at least one model is selected for each unit operation from a model repository. In an embodiment, the at least one model corresponds to: (i) a mechanistic model, (ii) an empirical model, (iii) a rule-based model, and (iv) a data-based model. In an embodiment, the at least one model is provided with a unique tag to activate at a same time. In an embodiment, the at least one control parameter from the model based control for at least one unit operation includes: (a) revised set-point of control parameters, (b) profiles of control parameters for a given time period. In an embodiment, the at least one control parameter from the recipe builder at a unit operation level includes one or more logics. In an embodiment, one or more logics corresponds to: (i) an operating space and an operating set point for each of the unit operations, (ii) an operating set point for each of process pumps, and (iii) expected normal operating modes for each of the unit operations. In an embodiment, the at least one pre-defined control parameter in the PLC at the unit operation level includes (i) an operating set points based on one or more standard specifications of the one or more equipments, and (ii) prior knowledge of the one or more equipments.

In another aspect, there is provided a system to control a continuous bioprocessing. The system includes a memory storing instructions; one or more communication interfaces; and one or more hardware processors coupled to the memory via the one or more communication interfaces, wherein the one or more hardware processors are configured by the instructions to: receive, at least input data associated with one or more equipments through a data historian; generate, by a recipe builder, a sequence of unit operations to determine at least one job order based on the at least input data associated with the one or more equipments for the at least one unit operation; obtain, at least one control decision associated with at least one control parameter based on the at least one job order; communicate, via the middleware, the at least one control decision associated with at least one control parameter to the PLC in a PLC readable format; and execute, by a control system of the PLC, the at least one control decision on a unit equipment to control: (i) a continuous bioprocessing train by the PLC, and (ii) an individual unit operation. The at least input data corresponds to one or more process variables associated with the one or more equipments and a data associated with at least one unit operation. The one or more process variables corresponds to (i) a pressure, (ii) a turbidity, (iii) a concentration, (iv) a conductivity, (v) a pH, (vi) a temperature, and (vii) a flow rate. The at least one job order is transferred to a programmable logic controller (PLC) for execution via a middleware. The at least one control decision is obtained based on at least one of: (i) a model based control, or (ii) a recipe based control, or (iii) at least one pre-defined control parameters in the PLC, or (iv) a combination thereof.

In an embodiment, the one or more equipments corresponds to: (i) a bioreactor, (ii) an acoustic wave separator (AWS), (iii) a near infra-red (NIR) spectroscopy, (iv) a high-performance liquid chromatography (HPLC), (v) continuous capture chromatography, (vi) viral inactivation unit, (vii) continuous polishing chromatography, (viii) pumps, (ix) ultrafiltration-diafiltration unit, (x) in-line turbidity sensors, (xi) conductivity sensors, and (xii) a soft sensor. In an embodiment, the soft sensor corresponds to at least one of: (a) a physics-based model, (b) a data-based model, and (c) a hybrid physics plus data-based model. In an embodiment, at least one model is selected for each unit operation from a model repository. In an embodiment, the at least one model corresponds to: (i) a mechanistic model, (ii) an empirical model, (iii) a rule-based model, and (iv) a data-based model. In an embodiment, the at least one model is provided with a unique tag to activate at a same time. In an embodiment, the at least one control parameter from the model based control for at least one unit operation includes: (a) revised set-point of control parameters, (b) profiles of control parameters for a given time period. In an embodiment, the at least one control parameter from the recipe builder at a unit operation level includes one or more logics. In an embodiment, one or more logics corresponds to: (i) an operating space and an operating set point for each of the unit operations, (ii) an operating set point for each of process pumps, and (iii) expected normal operating modes for each of the unit operations. In an embodiment, the at least one pre-defined control parameter in the PLC at the unit operation level includes (i) an operating set points based on one or more standard specifications of the one or more equipments, and (ii) prior knowledge of the one or more equipments.

In yet another aspect, there are provided one or more non-transitory machine readable information storage mediums comprising one or more instructions which when executed by one or more hardware processors causes at least one of: receiving, at least input data associated with one or more equipments through a data historian; generating, by a recipe builder, a sequence of unit operations to determine at least one job order based on the at least input data associated with the one or more equipments for the at least one unit operation; obtaining, at least one control decision associated with at least one control parameter based on the at least one job order; communicating, via the middleware, the at least one control decision associated with at least one control parameter to the PLC in a PLC readable format; and executing, by a control system of the PLC, the at least one control decision on a unit equipment to control: (i) a continuous bioprocessing train by the PLC, and (ii) an individual unit operation. The at least input data corresponds to one or more process variables associated with the one or more equipments and a data associated with at least one unit operation. The one or more process variables corresponds to (i) a pressure, (ii) a turbidity, (iii) a concentration, (iv) a conductivity, (v) a pH, (vi) a temperature, and (vii) a flow rate. The at least one job order is transferred to a programmable logic controller (PLC) for execution via a middleware. The at least one control decision is obtained based on at least one of: (i) a model based control, or (ii) a recipe based control, or (iii) at least one pre-defined control parameters in the PLC, or (iv) a combination thereof.

In an embodiment, the one or more equipments corresponds to: (i) a bioreactor, (ii) an acoustic wave separator (AWS), (iii) a near infra-red (NIR) spectroscopy, (iv) a high-performance liquid chromatography (HPLC), (v) continuous capture chromatography, (vi) viral inactivation unit, (vii) continuous polishing chromatography, (viii) pumps, (ix) ultrafiltration-diafiltration unit, (x) in-line turbidity sensors, (xi) conductivity sensors, and (xii) a soft sensor. In an embodiment, the soft sensor corresponds to at least one of: (a) a physics-based model, (b) a data-based model, and (c) a physics plus data-based model. In an embodiment, at least one model is selected for each unit operation from a model repository. In an embodiment, the at least one model corresponds to: (i) a mechanistic model, (ii) an empirical model, (iii) a rule-based model, and (iv) a data-based model. In an embodiment, the at least one model is provided with a unique tag to activate at a same time. In an embodiment, the at least one control parameter from the model based control for at least one unit operation includes: (a) revised set-point of control parameters, (b) profiles of control parameters for a given time period. In an embodiment, the at least one control parameter from the recipe builder at a unit operation level includes one or more logics. In an embodiment, one or more logics corresponds to: (i) an operating space and an operating set point for each of the unit operations, (ii) an operating set point for each of process pumps, and (iii) expected normal operating modes for each of the unit operations. In an embodiment, the at least one pre-defined control parameter in the PLC at the unit operation level includes (i) an operating set points based on one or more standard specifications of the one or more equipments, and (ii) prior knowledge of the one or more equipments.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
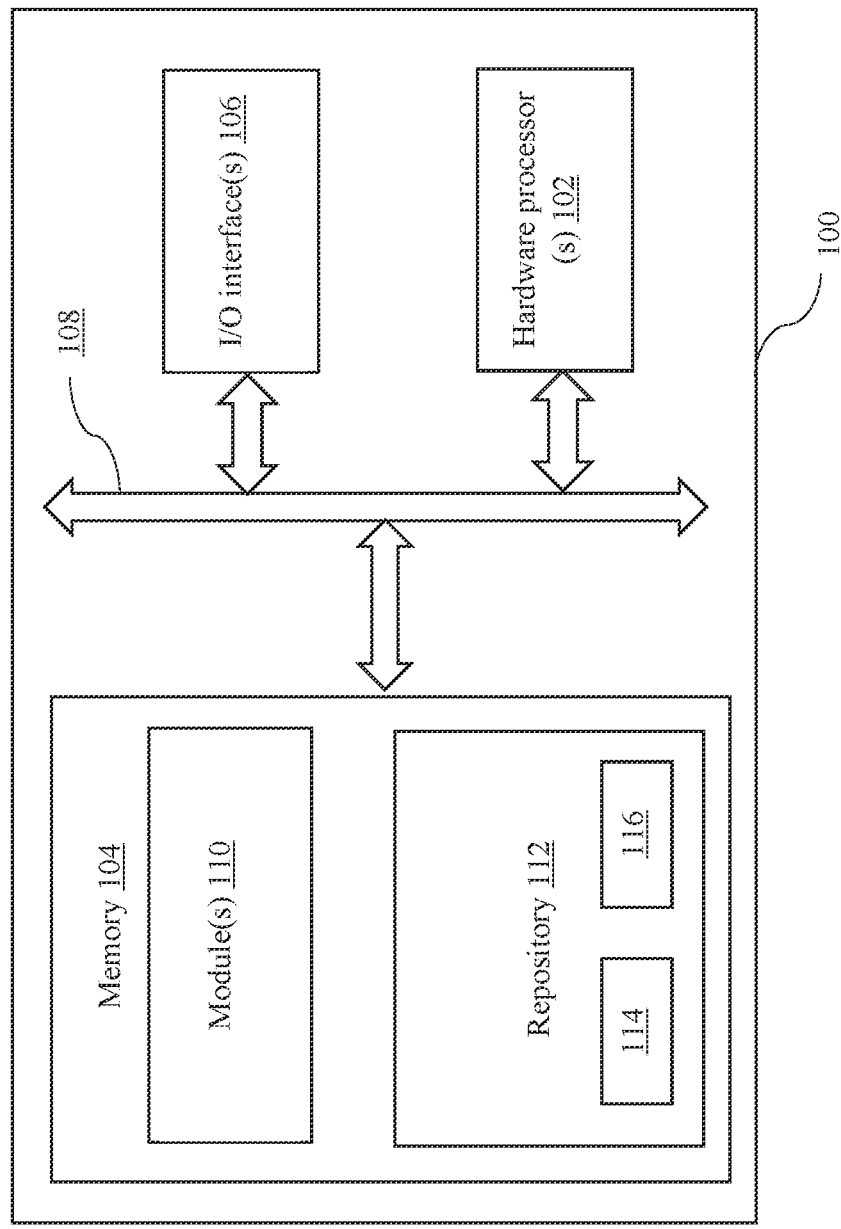
FIG. 1 illustrates a system to control a continuous bioprocessing plant, according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

The embodiments of the present disclosure herein disclose an integrated hardware and software control system i.e., a programmable logic controller (PLC) to control a continuous biomanufacturing train alongside pumps and a normal unit operation equipment for protein production, including clarification, chromatography, ultrafiltration-diafiltration, and depth filtration. The embodiments of the present disclosure herein specifically disclose a method of setting up a continuous platform of unit operations for end-to-end production and purification of biomolecules with an integrated controller covering one or more applications but not limited to a hardware-software communication, data collection, data recording, data storage, data historian, and control for optimization of performance and quality. The control system operates at four levels (a) a data acquisition and the data historian to record real time or periodic data from sensors in the continuous bioprocessing train, including but not limited to weight, pH, temperature, pressure, Ultraviolet (UV) spectroscopy, conductivity, pump revolutions per minute (RPM), and valve positions; (b) specifications for normal process operation for the unit operations including cleaning time, capacity, and normal operating spaces and limits for unit operations and process streams; (c) one or more customized algorithms, including mechanistic models or empirical models for optimizing process productivity and product quality; and (d) executing control decisions and includes the hardware-software integration of a controller computer with the different unit operations via open platform communications (OPC), Local area network (LAN), Python, Input/Output modules, or other hardware-software communication protocols.

Referring now to the drawings, and more particularly to FIGS. 1 through 5B, where similar reference characters denote corresponding features consistently throughout the figures, there are shown preferred embodiments and these embodiments are described in the context of the following exemplary system and/or method.

FIG. 1 illustrates a system 100 to control a continuous bioprocessing plant, according to some embodiments of the present disclosure. In an embodiment, the system 100 includes one or more processor(s) 102, communication interface device(s) or input/output (I/O) interface(s) 106, and one or more data storage devices or memory 104 operatively coupled to the one or more processors 102. The memory 104 includes a database. The one or more processor(s) processor 102, the memory 104, and the I/O interface(s) 106 may be coupled by a system bus such as a system bus 108 or a similar mechanism. The system 100 is further connected via the V/O interface(s) 106. The one or more processor(s) 102 that are hardware processors can be implemented as one or more microprocessors, microcomputers, microcontrollers, digital signal processors, central processing units, state machines, logic circuitries, and/or any devices that manipulate signals based on operational instructions. Among other capabilities, the one or more processor(s) 102 is configured to fetch and execute computer-readable instructions stored in the memory 104. In an embodiment, the system 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like. The I/O interface device(s) 106 may include a variety of software and hardware interfaces, for example, interfaces for peripheral device(s), such as a keyboard, a mouse, an external memory, a camera device, and a printer. Further, the I/O interface device(s) 106 may enable the system 100 to communicate with other devices, such as web servers and external databases. The I/O interface device(s) 106 can facilitate multiple communications within a wide variety of networks and protocol types, including wired networks, for example, local area network (LAN), cable, etc., and wireless networks, such as Wireless LAN (WLAN), cellular, or satellite. In an embodiment, the I/O interface device(s) 106 can include one or more ports for connecting number of devices to one another or to another server.

The memory 104 may include any computer-readable medium known in the art including, for example, volatile memory, such as static random-access memory (SRAM) and dynamic random-access memory (DRAM), and/or non-volatile memory, such as read only memory (ROM), erasable programmable ROM, flash memories, hard disks, optical disks, and magnetic tapes. In an embodiment, the memory 104 includes a plurality of modules 110 and a repository 112 for storing data processed, received, and generated by the plurality of modules 110. The plurality of modules 110 may include routines, programs, objects, components, data structures, and so on, which perform particular tasks or implement particular abstract data types.

Further, a database in the repository 112 stores information pertaining to inputs fed to the system 100 and/or outputs generated by the system (e.g., data/output generated at each stage of the data processing) 100, specific to the methodology described herein. More specifically, the database stores information being processed at each step of the proposed methodology.

Additionally, the plurality of modules 110 may include programs or coded instructions that supplement applications and functions of the system 100. The repository 112, amongst other things, includes a system database 114 and other data 116. The other data 116 may include data generated as a result of the execution of one or more modules in the plurality of modules 110. Further, the database stores information pertaining to inputs fed to the system 100 and/or outputs generated by the system (e.g., at each stage), specific to the methodology described herein. Herein, the memory for example the memory 104 and the computer program code configured to, with the hardware processor for example the processor 102, causes the system 100 to perform various functions described herein under.

Figure 2A:
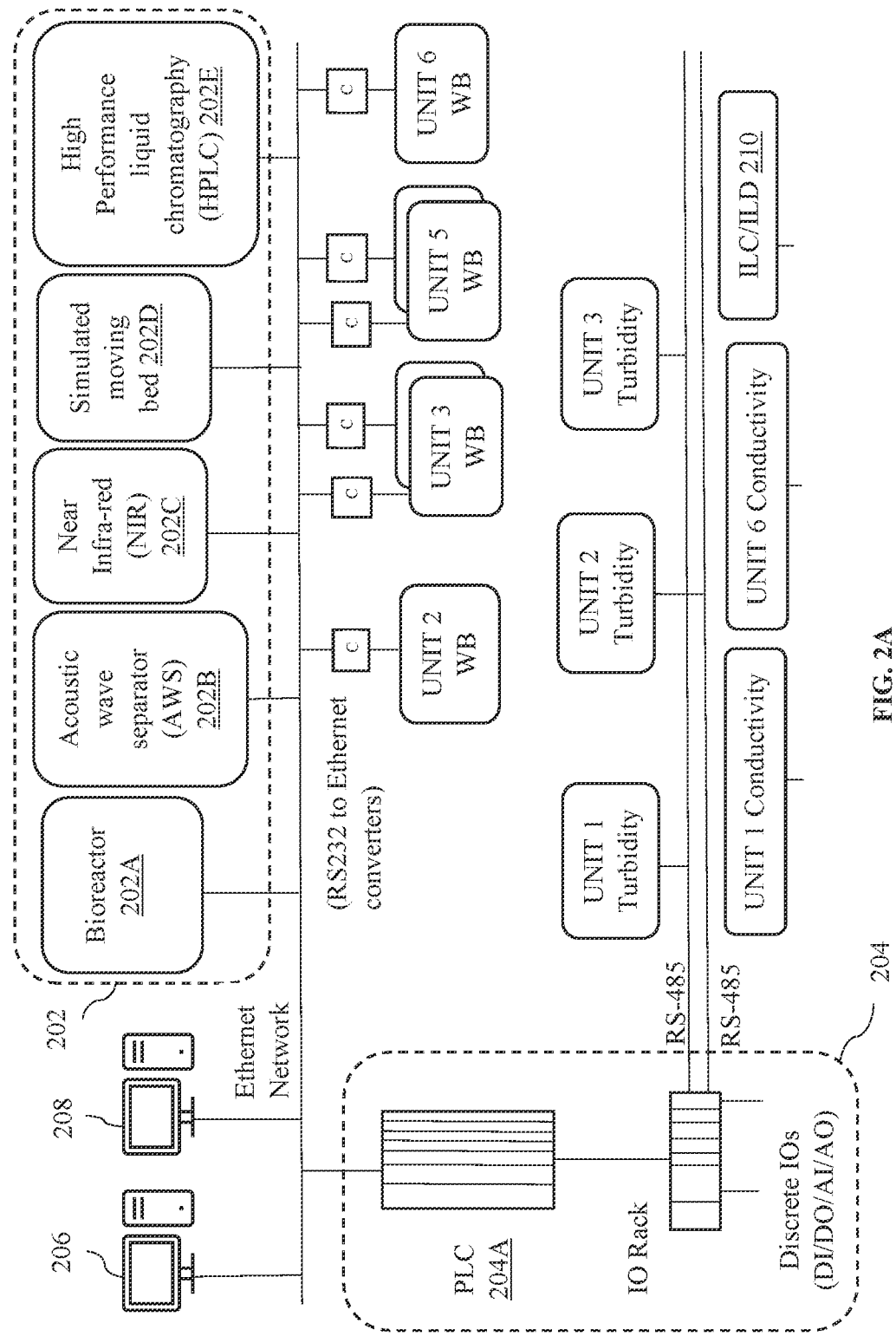
FIG. 2A and FIG. 2B are exemplary functional block diagrams illustrates a hardware-software integration in the system as depicted in FIG. 1, according to some embodiments of the present disclosure.
Figure 2B:
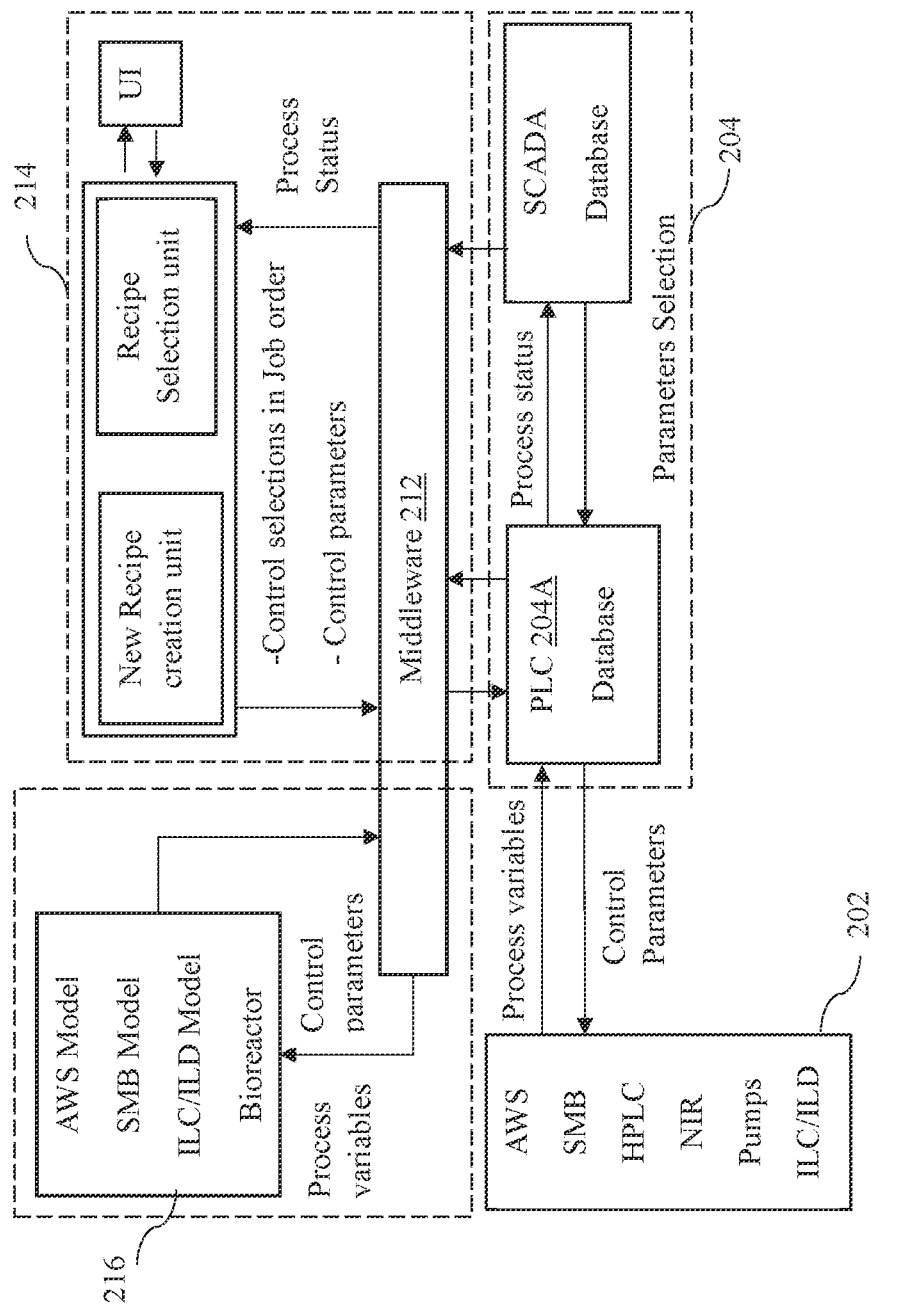

FIG. 2A and FIG. 2B are exemplary functional block diagrams illustrates a hardware-software integration in the system 100 as depicted in FIG. 1, according to some embodiments of the present disclosure. The system 100 includes one or more equipments 202, a control system 204, an engineering station 206, a data historian 208, an ultrafiltration-diafiltration unit (UF-DF) 210, a middleware 212, a recipe builder 214, and a model repository 216. The one or more equipments 202 further include a bioreactor 202A, an acoustic wave separator (AWS) 202B, a near infra-red (NIR) spectroscopy unit 202C, a simulated moving bed (SMB) 202D, a high-performance liquid chromatography (HPLC) unit 202E. The control system 204 further include the programmable logic controller (PLC) 204A. The UF-DF is performed using an inline concentrator (ILC)—an inline dilution (ILD) unit 210. In an embodiment, the UF-DF unit 210 are interchangeably referred as the ILC/ILD unit 210. The system 100 includes four components: (a) data acquisition and recording, (b) a Middleware-logic, (c) Middleware-algorithms and (d) execution of one or more control actions. In an embodiment, the middleware-logic is alternatively referred as the recipe builder 214. Similarly, the middleware-algorithm is alternatively referred as the model repository 216. A controller receives one or more process variables as an input. In an embodiment, the controller may be referred to at least one of a computer or the programmable logic controller (PLC) 204A running on any language or combination of languages, for example Python, R, or Ladder Logic. In an embodiment, one or more layers are developed over a unit operations equipment without the direct OPC control to facilitate a read and a write control. In an embodiment, online measurements of flowrates, pH, etc are available at high frequencies.

The data historian 208 through which data is acquired based on the unit operation and one or more process variables that is being recorded, and with one or more sensors. In an embodiment, the one or more sensors is configured to measure the one or more process variables. For example, the one or more sensors corresponds to a hardware sensor or a soft sensor. In an embodiment, the soft sensor is alternatively referred as a software sensor. In an embodiment, the soft sensor corresponds to at least one of: (a) a physics-based model, or (b) data-based model, or (c) a hybrid physics plus data-based model that predicts numerical values of one or more parameters for which a hardware sensor is not available. For example, intermediate protein concentrations in a plant can be predicted in a real time using the soft sensor without having to wait for one or more experimental measurements from a laboratory. In an embodiment, the data is stored on the data historian 208 as text files. The data acquisition and the recording, in which data of the acoustic wave separator (AWS) 202B includes flowrates of one or more pumps (e.g., five pumps) and turbidities of one or more chambers (e.g., four chambers) which are auto exported at fixed intervals.

In an embodiment, a data of a continuous chromatography includes flowrates and pressures of seven pumps as well as pH, UV, and conductivity data from eight sensors, which are saved on the PLC 204A via OPC read commands. A data of the bioreactor 202A includes an agitation speed, an air sparging rate, a feed flow rate, a concentration, a dissolved oxygen concentration, a nutrient concentration, a pH data from one or more sensors that are connected to the PLC 204A via RS-232. The ultrafiltration-diafiltration (UF-DF) unit 210, in which one or more pumps used to supply a feed and a buffer solutions are connected to a PC via RS-232 cable and a flowrate data was recorded into a text file at fixed intervals. In an embodiment, for each of the two depth filtration steps, the three-way solenoid valve and the in-line pressure sensors are connected to the PLC 204A, with the valve position and a pressure data recorded in a text file at fixed intervals. For a viral inactivation step, an in-line pH sensor was connected to the PLC 204A via RS-232. In an embodiment, the PCs are all interconnected via a local area network (LAN) and the files are saved in a shared folder on the LAN network as well as on the PLC 204A. For an analytical equipment, data associated with the near Infrared (NIR) spectroscopy unit 202C is stored in a real time and accessed by the PLC 204A. The at-line high performance liquid chromatography (HPLC) unit 202E chromatograms are auto-integrated and stored in a real time and accessed by the PLC 204A.

With reference to FIG. 2B, a process for continuous biopharma manufacturing is initiated for which, the recipe builder 214 provides a platform. The recipe builder 214 provides a user interface (UI) for the user to set up the process. The user can set initial parameters for different unit operations by the recipe builder 214 and can create a sequence of the unit operations. The user can perform following steps: (a) provides a name of a product, description of the product (E.g., Mab solution, Yeast solution); (b) provides a name of one or more equipments and list them which are required in whole process e.g., the bioreactor 202A, the acoustic wave separator (AWS) 202B, the SMB 202D, the high-performance liquid chromatography (HPLC) unit 202E, the ILC/ILD unit 210. A functionality is provided to create sub-assemblies for the equipment e.g., in the SMB 202D there are sub-assembles like pumps, valves etc; (c) create one or more major unit operations that are needed in the process e.g., fermentation, separation of one or more impurities, a chromatography, a viral inactivation, and the ultrafiltration-diafiltration (UF-DF) unit 210. The user can set one or more control parameters which are required to start each unit operation. e.g., for acoustic wave separation, the one or more control parameters are turbidity, feed flow rate, recirculation flow rate—the initial values of the control parameters are set up during this stage; (d) listing out one or more actions required in each unit operations such as in chromatography, there are multiple actions such as a loading, a washing, a cleaning, an equilibration, an elution. For example, the user can specify a sequence of the actions as well as associated timings like loading to be performed for sixty mins, then washing for 20 mins etc; (e) create the sequence of the unit operations and actions. e.g., a typical process starts with the fermentation which requires the bioreactor 202A, then separation which requires the AWS 202B, then the chromatography which requires the SMB 202D as a sequence of steps is created which is referred as a recipe and the recipe is transferred to the PLC 204A for execution; and (f) create a job order upon creating the recipe. The user can perform at least one of (i) provide a job name, (ii) select a mode of operation for control i.e., one or more predefined setpoints in the PLC 204A, a recipe based control, a model based control, (iii) select a unit operation model, which is to be activated for the process, and (iv) select the recipe in presence of multiple recipes. After the job is created, the job is transferred to the PLC 204A for execution via the middleware 212.

In an embodiment, once the recipe is created, the user selects a particular recipe according to the process from a list of multiple recipes created for different processes. The data from the recipe builder 214 is transferred to the PLC 204A for further processing by the middleware 212. In an embodiment, the middleware 212 acquired parameters and instructions from the recipe builder 214 and the models, are sent to the PLC 204A/the data historian 208. The middleware 212 parses the data received from the recipe and the models, are converted into a PLC readable format, and writes the data to the PLC 204A. In an embodiment, the middleware 212 maps the one or more process variables and one or more values present in the data to a PLC database. For example, if there is a pump (P1) with a speed (S1), then the P1 is mapped to an address in the PLC database, and similarly, S1 is mapped to another address. After writing the data to the PLC 204A, the middleware 212 communicates an acknowledgement to the recipe builder 214.

The model repository 216 also includes a selection of one or more mechanistic models, one or more empirical models, or one or more rule-based models, or one or more data-based models for control at a unit operation level. In an embodiment, control at the unit operation level is also performed based on a data shared by the recipe builder 214. The data shared by the recipe builder 214 include operating space and operating set point for each unit operation, operating set point for each of the process pumps, and expected normal operating modes for each of the individual unit operations. Each model in the model repository 216 is provided with a unique tag, and one or more models are activated at same time. The functionality to turn a model-based control 'on' or 'off' at any point during the process for any unit operation is inbuilt into the model repository 216 by providing each model a hierarchy in the control structure to prevent conflicts.

A hierarchy of a model can be a low or a medium or a high priority. An input for the one or more models is the data stored in the data historian 208, continuously added to at fixed time intervals from the data acquisition layer. The model repository 216 also includes one or more control algorithms required in the process. The selection of control algorithms is decided based on the models selected for the control. In an embodiment, the middleware 212, the one or more models in the model repository 216, one or more logics in the recipe builder 214 are written in any software coding language, including but not limited to ladder logic, Python, R, and MATLAB. The middleware 212 also enable a handshake between the programmable logic controller (PLC) 204A/the data historian 208 for a read and a write operation.

An AWS model in the model repository 216 includes an approach to adjust an acoustic power and a feed flow rate to maximize a cell separation efficiency (CSE) and a yield. In an embodiment, one or more inputs to the AWS models are the acoustic power, the feed flow rate, cell load density in the feed. The AWS model converts an inline turbidity measurement to a cell density or a cell concentration in AWS chamber wherever an inline turbidity sensors are available. The AWS model predicts the CSE using the feed flowrate, inline turbidity measurements of feed stream, and the acoustic power, along with the cell concentration. The AWS model may be a databased model or a physics-based model or a combination of both, which in turn is used for determining the CSE. For example, the data based models such as a machine learning and deep learning models are used for prediction of the CSE. The physics-based model includes models such as a population balance model to determine number density of cells. A comprehensive AWS model using the data based and/or the physics-based model can determine the CSE with a high accuracy. The CSE can be determined for an individual chamber or for all chambers as required. The CSE determined for the individual chambers can together contribute to overall CSE of the AWS process.

In an embodiment, a capture chromatography models in the model repository 216 are configured to modify a column loading and elution to maximize resin utilization and elution consistency. The polishing chromatography models are configured to modify the loading or elution conditions to maximize separation. One or more inputs of the polishing chromatography models are one or more elution profiles from the capture chromatography, a feed velocity, and a pressure data. The polishing chromatography model converts inline NIR measurements to the one or more elution profiles. The polishing chromatography model predicts a chromatogram of charge variants in a product using the one or more elution profiles from the capture chromatography, the feed velocity, and the pressure data. In an embodiment, the polishing chromatography model may be a databased model or a physics-based model or a combination of both, which in turn is used for determining the chromatogram.

For example, the data based models such as a machine learning and deep learning models are used for prediction of the chromatogram. The physics-based model includes models such as a transport dispersive model to predict concentration of the charge variants in the product. A comprehensive polishing chromatography model using the data based and/or the physics-based model can determine the concentration of the charge variants in the product with a high accuracy. Using the predicted chromatogram, a start and a stop time of pooling are estimated such that the maximum separation of charge variants is achieved. In an embodiment, other attributes such as yield, and impurities are also considered while estimating the start and stop time at the pooling step.

Ultrafiltration and diafiltration (UF-DF) models or ILC/ILD models in the model repository 216 are configured to modify the feed, permeate and retentate flow rates and pressures to maximize the concentration of the protein up to a desired concentration factor and limits a composition of excipients in a final formulation. The inputs to the UF-DF model or the ILC/ILD model are feed flowrate and transmembrane pressure and outputs for the model are volumetric concentration factor (VCF) or product concentration. The volumetric concentration factor (VCF) is a ratio of the initial feed concentration to the final product concentration. The UF-DF model or the ILC/ILD model converts the inline conductivity measurements to a concentration of protein of interest wherever inline conductivity sensors are available. The UF-DF model or the ILC/ILD model predicts the VCF or a product concentration using a pressure data, a feed flow rate, and the concentration of protein of interest in the feed flow stream. The UF-DF model or the ILC/ILD model may be a databased model or physics-based model or a combination of both, which in turn is used for determining the VCF or the product concentration. For example, the data based models such as machine learning and deep learning models are used for the VCF or for prediction of the product concentration. The physics-based model includes models such as a gel-polarization model to determine ultrafiltration flux. A comprehensive UF-DF model or ILC/ILD model using the data based and/or the physics-based model can determine the VCF or the product concentration with a high accuracy.

In an embodiment, multiple models in the model repository 216 are present for each unit operation, including a mechanistic, an empirical, a rule based, and a data-based model. The empirical models utilize equations derived from one or more experiments to take in a real time data, process mathematically using a series of linear or nonlinear equations and provide predictions of quality attributes as an output which were used to modify the process parameters of the unit operations. The mechanistic models utilize differential or fundamental equations to predict a condition of an operation output in terms of efficiency, purity, or yield, based on the current process parameter inputs. In an embodiment, the rule-based models are based on experimental thresholds and provided different control logic based on a status of a different process parameters. The data-based models are built by training either machine learning or deep learning algorithms with the historical data.

Figure 3:
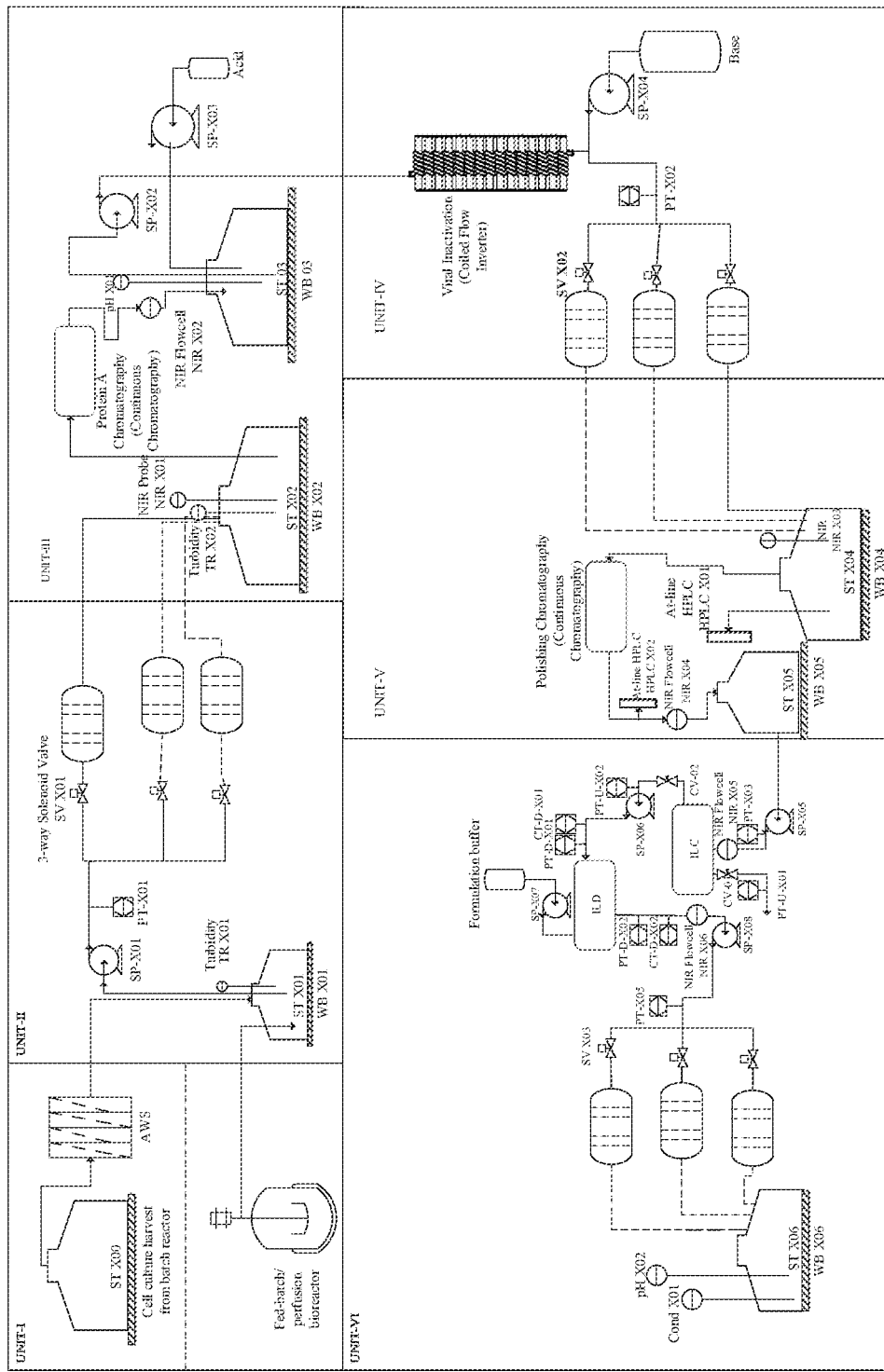
FIG. 3 is an exemplary block diagram with one or more units to control the continuous bioprocessing plant, according to some embodiments of the present disclosure.

FIG. 3 is an exemplary block diagram with one or more units to control the continuous bioprocessing plant, according to some embodiments of the present disclosure. A unit I include a surge tank I (STX00). The material from the bioreactor 202 is stored and sent to the acoustic wave separator (AWS) 202B for clarification of the material. A unit II consists of a surge tank II (STX01) placed over a weighing balance (WBX01) followed by a pump (SPX01), a pressure transmitter (PT-X01), one or more solenoid valves (SV X01) and a depth filter. The PT-X01 measures a pressure across membrane of the depth filter which monitors a membrane pressure and thereby fouling. The SV-X01 is a three-way valve that switches a flow of the material from one depth filter to another depth filter. A turbidity probe (TR-X01) is inserted in the ST-X01 to monitor the incoming fed material turbidity from the AWS 202B. A unit III include a surge tank 2 (ST X02) with a weighing balance (WB-X02) combination followed by a continuous chromatography equipment for capture chromatography (protein A), a surge tank 3 (ST03) with a weighing balance (WB-03) and pumps SP-X02 for pumping the material from the ST03 and a pump SP-X03 to pump an acid to next unit operation. A turbidity probe (TR X02) and a pH probe (pH X01) are placed in a ST X02 and the ST03 respectively along with a NIR probe (NIR X01) in the ST X02 and an inline NIR flow cell (NIR X02) after the continuous capture chromatography to measure concentrations.

A unit IV include a coiled flow inversion reactor (CFIR) for a viral activation followed by a pump SP-X04 to a pump base to output of the CFIR for neutralization. Further, a pressure transmitter (PT-X02), a solenoid valve (SV-X02) and the depth filters are placed for clarification. A unit V include a surge tank (ST X04) with a weighing balance (WB X04) set up that receives the material from the unit IV followed by the continuous chromatography for polishing chromatography and a surge tank (ST X05) with a weighing balance (WB X05). Here, the at-line HPLCs unit 202E are placed before a HPLC X01 and after a HPLC X02 continuous polishing chromatography to measure a percentage charge variant/aggregate in feed and elute respectively along with a NIR flow cell (NIR X04) to measure a concentration.

A unit VI, a pump SP-X05 which pumps the material from the ST-X05 to the filtration unit through a NIR flow cell (NIR X05) which measures a concentration. Filtration unit include an inline concentrator (ILC) membrane module, an inline dilution (ILD) membrane module, three pumps (SP X06, SP X07, SP X08), two pressure transmitters for ultrafiltration (PT-U-X01, PT-U-X02), two pressure transmitters for diafiltration (PT-D-X01, PT-D-X02), two control valves (CV-01, CV-02) and two conductivity transmitters for diafiltration (CT-D-X01, CT-D-X02). The ILC concentrates the incoming material by a volume reduction and the ILD for formulation buffer exchange. This setup is followed by a NIR flow cell (NIR X06) to measure a final formulated product concentration which is finally passed through one or more set of depth filters with a pressure transmitter (PT X05) and the solenoid valve (SV X03) to the surge tank (ST X06) and a weighing balance (WB X06), where pH (pH X02) and a conductivity probes (cond X01) measure a final product quality at consistent manner.

Figure 4:
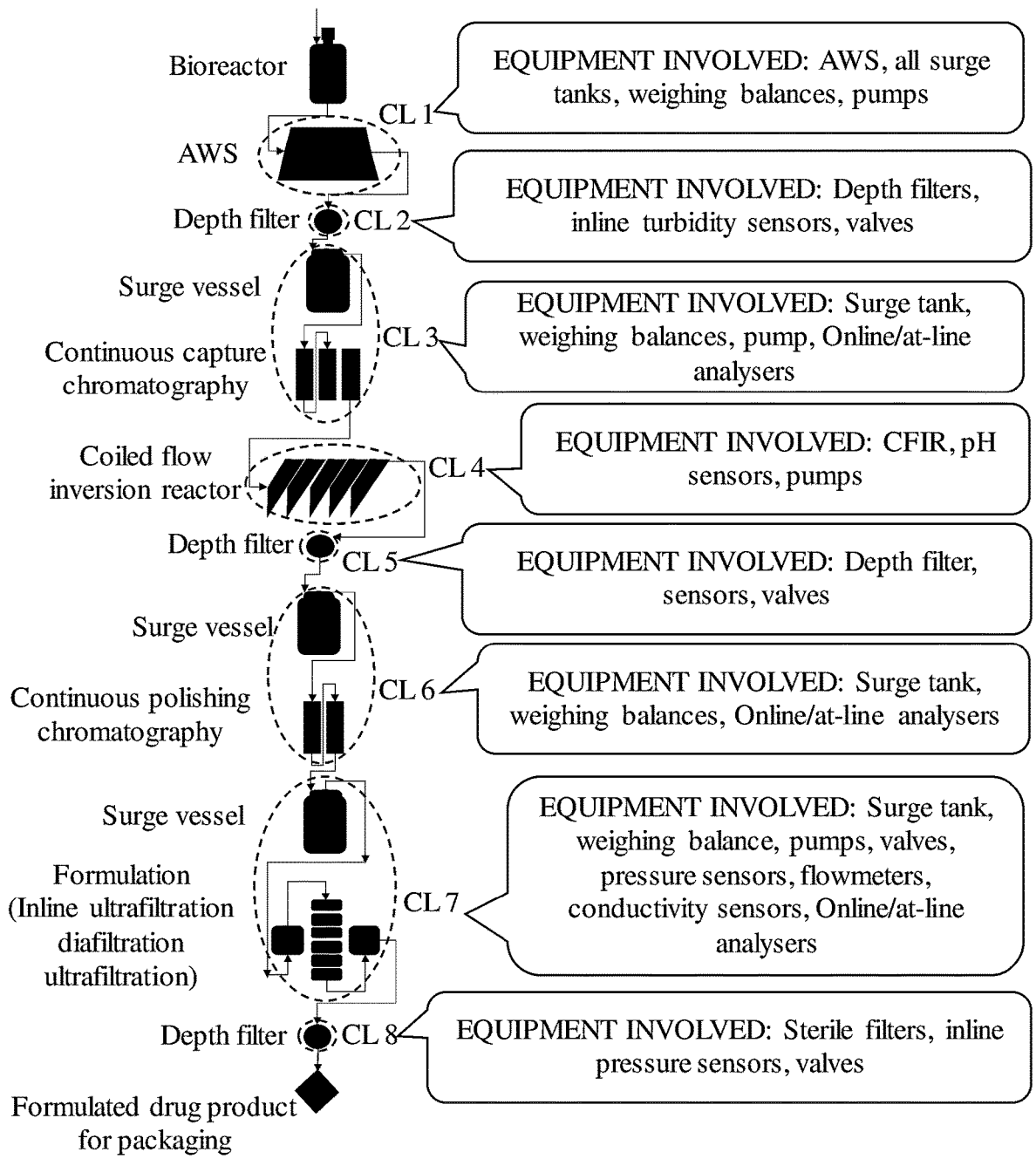
FIG. 4 is an exemplary flow diagram illustrating a control strategy solution showing one or more control loops for a continuous downstream processing, according to some embodiments of the present disclosure.

FIG. 4 is an exemplary flow diagram illustrating the control strategy solution showing the one or more control loops for the continuous downstream processing, according to some embodiments of the present disclosure. A centralized control of an integrated continuous bioprocessing is carried out using one or more control decisions taken for the entire plant and/or individual equipment. This is achieved by integrating with one or more control loops (CL1-CL8) in the continuous bioprocessing train. The one or more control decisions of one or more control parameters in one or more control loops are obtained using at least one of: (i) model-based control, (ii) receiving control parameters from the recipe builder 214, (iii) using one or more pre-defined control parameters available in the PLC 204A. A mode of control is obtained as a control selection in the one or more job orders generated by the recipe builder 214. In an embodiment, solution of a model-based control can be a single or multiple set point (s) for a steady state model or one or more profiles of one or more control parameters for a given time-period for a dynamic model. The one or more control parameters available in the PLC 204A at the unit operation level includes operating set-points based on standard specifications of the one or more equipments and prior knowledge of the one or more equipments. The abovementioned methods are utilized for obtaining one or more control decisions in the one or more control loops (CL1-CL8) in the continuous bioprocessing train.

A control loop 1 (CL1), involves the AWS, the surge tank 1, the weighing balance and the pump. The CL1 controls the feed pumps for flow rate and the acoustic power to improve the CSE of the AWS 202B. The acoustic power being below a threshold value which leads to escape of cells and reduce cell separation efficiency likewise, high flow rate leads to cell movement in the direction of streamlines and cells escape from the acoustic field. Hence, optimum set points of the flow rate and the acoustic power are determined such that the flow rate and the acoustic power are under respective threshold values. The CL1 also controls the feed pumps and the acoustic power controls to stop the process when spikes in the turbidity measurements are observed.

A control loop 2 (CL2) involves depth filters, inline turbidity sensors and valves. The control loops are configured to monitor depth filtration efficiency after the AWS 202B to ensure that an outlet turbidity is below a desired threshold and automate filter change or a trigger alarm when turbidity breakthrough occurs. A control loop 3 (CL3) involves a surge tank 2, a weighing balance, pumps, the capture chromatography, online/atline analyzers (NIRS, HPLC, Fourier-transform Infrared (FTIR), UV, etc.). In the CL3, control of the capture chromatography, Protein A, is conducted to ensure proper scheduling of multi-column operation and monitor loading or breakthrough using advanced analyzers like NIRS or UV for achieving better resin utilization so that product loss is prevented. A control loop 4 (CL4) involves CFIR, pH sensors and acid/base pumps to control pH for the viral inactivation in CFIR. The pH is lowered by the addition of acid at entrance of the CFIR, and then raised by addition of base at the CFIR exit by using the acid and base pumps in a PID control loop with online pH sensors. However, if pH values exceed critical limits, thereby affecting a product stability, and alarms are triggered when the pH measurements exceed pre-defined critical limits.

A control loop 5 (CL5) involves depth filters, inline pressure sensor, and valves as similar to the CL2 which is configured to monitor depth filtration after low pH hold in the CFIR to ensure outlet turbidity is below a desired threshold and automates filter change or triggers an alarm when turbidity breakthrough occurs. A control loop 6 (CL6) involves a surge tank 3, a weighing balance, pumps, continuous polishing chromatography, online/atline analyzers (NIRS, HPLC, FTIR, UV, etc.) for polishing chromatography. The CL6 controls polishing step (Cation exchange chromatography (CEX), Anion exchange chromatography (AEX), Hydrophobic interaction chromatography (HIC), Multimodal) to ensure proper scheduling of multi-column operations. For example, advanced analyzers like NIRS or UV can be used for monitoring load and elution quality attributes like aggregate content, charge variant content, or concentration in real time for optimal pooling decisions.

A control loop 7 (CL7) involves formulation unit, surge tank weighing balance, pumps, control valves, pressure sensors, flow meters, conductivity sensors, online/atline analyzers (e.g., NIRS, UV, etc.). The CL7 controls ultrafiltration using flux-based or TMP-based control with inline pressure sensors and flow meters to ensure the target product concentration is achieved. The CL7 controls diafiltration by ensuring a correct number of diavolumes are supplied in each pass to achieve target concentrations of excipients in the final formulation. For example, advanced analyzers like NIRS or UV are used for monitoring the concentration of product and excipients and for making control decisions. The weighing balance acts as a check for the membrane flow rates. Pressure sensors act as checks for membrane module integrity.

A control loop 8 (CL8) involves sterile filters, inline pressure sensor, valves that monitors a sterile filtration of formulated drug product. In an embodiment, one or more control loops include independent goals and can operate at a same level in a control structure hierarchy without conflicts. The weighing balances acts as a check for a loading step to prevent air from entering the column in case the prior surge tank is empty. For example, real time multivariate data analysis (MVDA) algorithms are implemented for predictive control or identifying process deviations. In an embodiment, execution of control decisions on the unit equipment is performed through the PLC 204A and the automation layer. In an embodiment, the PLC 204A acts on the data received from the middleware 212 and stores the data in a supervisory control and data acquisition (SCADA) and the data historian 208. The control decisions from the middleware 212 are transferred back to the PLC 204A and executed on the unit operation equipment through direct actuation through a PLC wiring, through the unit operation OPCs, or through automation layers over the existing unit operation software interfaces.

Figure 5A:
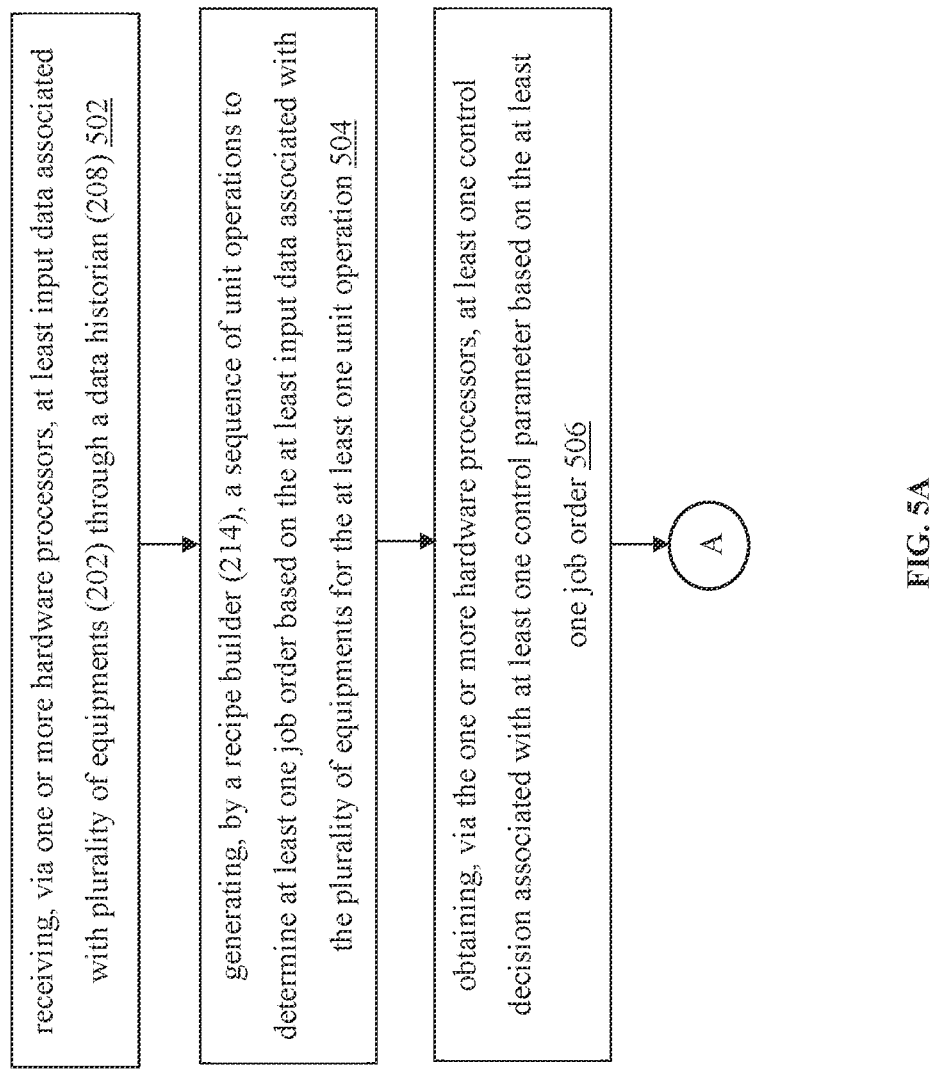
FIG. 5A and FIG. 5B are exemplary flow diagrams illustrating a method of controlling the continuous bioprocessing plant, according to some embodiments of the present disclosure.
Figure 5B:
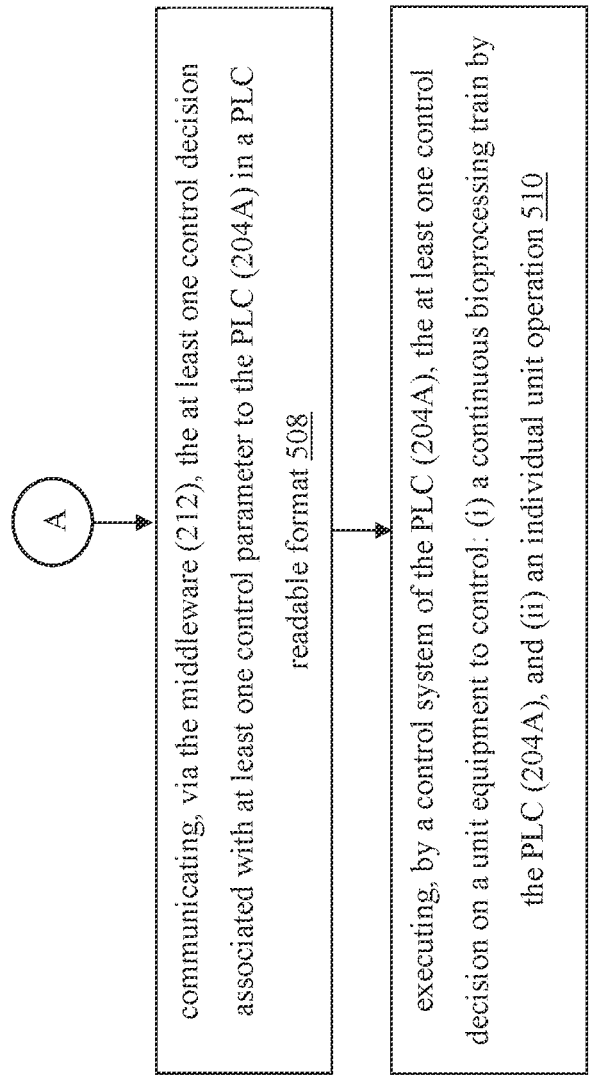

FIG. 5A and FIG. 5B are exemplary flow diagrams illustrating a method (500) of controlling the continuous bioprocessing plant, according to some embodiments of the present disclosure. In an embodiment, the system 100 comprises one or more data storage devices or the memory 104 operatively coupled to the one or more hardware processors 102 and is configured to store instructions for execution of steps of the method by the one or more processors 102. The flow diagram depicted is better understood by way of following explanation/description. The steps of the method of the present disclosure will now be explained with reference to the components of the system as depicted in FIGS. 2A and 2B.

At step 502, at least input data associated with one or more equipments 202 through the data historian 208 is received. The at least input data corresponds to the one or more process variables associated with the one or more equipments 202 and a data associated with at least one unit operation. The one or more process variables corresponds to (i) a pressure, (ii) a turbidity, (iii) a concentration, (iv) a conductivity, (v) a pH, (vi) a temperature, and (vii) a flow rate. The one or more equipment 202 corresponds to: (i) the bioreactor 202A, (ii) the acoustic wave separator (AWS) 202B, (iii) the near infra-red (NIR) spectroscopy unit 202C, (iv) the high-performance liquid chromatography (HPLC) unit 202E, (v) the continuous capture chromatography, (vi) the viral inactivation unit, (vii) the continuous polishing chromatography, (viii) the pumps, (ix) ultrafiltration-diafiltration unit 210, (x) the in-line turbidity sensors, (xi) conductivity sensors, and (xii) the soft sensor. The soft sensor corresponds to at least one of: (a) a physics-based model, and (b) a data-based model.

At step 504, by a sequence of unit operations is generated by the recipe builder 214 to determine at least one job order based on the at least input data associated with the one or more equipments 202 for the at least one unit operation. The at least one job order is transferred to the programmable logic controller (PLC) 204A for execution via the middleware 212. At step 506, at least one control decision associated with at least one control parameter is obtained based on the at least one job order. The at least one control decision is obtained based on at least one of: (i) a model based control, or (ii) a recipe based control, or (iii) at least one pre-defined control parameters in the PLC 204A, or (iv) a combination thereof. At step 508, the at least one control decision associated with at least one control parameter is communicated to the PLC (204A) via the middleware (212), in a PLC readable format. At step 510, the at least one control decision is executed by a control system of the PLC 204A on a unit equipment to control of: (i) a complete continuous bioprocessing train by the PLC 204A, and (ii) an individual unit operation.

At least one model is selected for each unit operation from a model repository 216. the at least one model corresponds to: (i) a mechanistic model, (ii) an empirical model, (iii) a rule-based model, and (iv) a data-based model. The at least one model is provided with a unique tag to activate at a same time. In an embodiment, the at least one control parameter from the model based control for at least one unit operation includes: (a) revised set-point of control parameters, (b) profiles of control parameters for a given time period. In an embodiment, the at least one control parameter from the recipe builder 214 at a unit operation level includes one or more logics. The one or more logics corresponds to: (i) an operating space and an operating set point for each of the unit operations, (ii) an operating set point for each of process pumps, and (iii) expected normal operating modes for each of the unit operations. In an embodiment, the at least one pre-defined control parameter in the PLC 204A at the unit operation level includes: (i) an operating set points based on one or more standard specifications of the one or more equipments 202, and (ii) prior knowledge of the one or more equipments 202.

The embodiments of present disclosure herein provide an integrated platform for plant wide operations that helps monitoring, control and diagnosis of the continuous biomanufacturing process. The embodiments of present disclosure herein with a global controller system for an entire plant which allows the unit operations are freely operated at corresponding optimized levels and errors are handled over long continuous campaigns without manual intervention or human supervision. The embodiments of present disclosure herein provide a robust and flexible control of continuous downstream purification trains for one or more biopharmaceutical products using the PLC and the data historian alongside the normal unit operations of protein production, including acoustic wave separation (AWS) system, bioreactor, chromatography, ultrafiltration, and depth filtration. The embodiments of present include the automation layer and the middleware which consider input operating parameters for different unit operations, such as flowrates, cycle times, pause times, and cleaning schedules to carry out normal operation of the continuous bioprocessing train and each of the individual unit operations with help of the PLC and the distributed control system. The embodiments of present disclosure herein augment the controller algorithm with additional mechanistic models and include logic for an automated model-based control for the continuous bioprocessing train and each of the individual unit operations.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method, comprising:
receiving, via one or more hardware processors, at least input data associated with one or more equipments through a data historian, wherein the one or more equipments includes a bioreactor, an acoustic wave separator (AWS), a near infra-red (NIR) spectroscopy unit, a simulated moving bed (SMB), a high-performance liquid chromatography (HPLC) unit, wherein the at least input data corresponds to one or more process variables associated with the plurality of equipments and a data associated with at least one unit operation of protein production including an acoustic wave separation (AWS) system, a chromatography, an ultrafiltration, a depth filtration, a fermentation, separation of one or more impurities, a viral inactivation, and an ultrafiltration-diafiltration (UF-DF) unit, and wherein the one or more process variables corresponds to (i) a pressure, (ii) a turbidity, (iii) a concentration, (iv) a conductivity, (v) a pH, (vi) a temperature, and (vii) a flow rate;
generating, by a recipe builder via the one or more hardware processors, a sequence of unit operations to determine at least one job order created upon creating a recipe, based on the at least input data associated with the plurality of equipments for the at least one unit operation, and wherein the at least one job order is transferred to a programmable logic controller (PLC) for execution via a middleware, wherein the middleware parses data received from the recipe, the middleware converts the parsed data into a PLC readable format, the middleware writes the data to the PLC, wherein the middleware maps the one or more process variables and one or more values present in the data to a PLC database and after writing the data to the PLC, the middleware communicates an acknowledgement to the recipe builder;

obtaining, via the one or more hardware processors, at least one control decision associated with at least one control parameter based on the at least one job order, and wherein the at least one control decision of one or more control parameters in one or more control loops is obtained based on at least one of: (i) a model based control in which a solution of the model-based control is a single set point or multiple set points for a steady state model or one or more profiles of the one or more control parameters for a time-period for a dynamic model, or (ii) receiving control parameters from the recipe builder or (iii) using at least one pre-defined control parameter available in the PLC, or (iv) a combination thereof;

communicating, via the middleware via the one or more hardware processors, the at least one control decision associated with the at least one control parameter to the PLC in a PLC readable format, wherein a centralized control of an integrated continuous bioprocessing is carried out with the at least one control decision taken for a unit bioprocessing plant and/or individual equipment by integrating with the one or more control loops in a continuous bioprocessing train; and executing, by a control system of the PLC via the one or more hardware processors, the at least one control decision on a unit operation equipment through direct actuation with a PLC wiring, through the unit operation open platform communications (OPCs), or through automation layers over existing unit operation software interfaces to control: (i) the continuous bioprocessing train by the PLC, and (ii) an individual unit operation.

2. The processor implemented method as claimed in claim 1, wherein the plurality of equipments corresponds to: (i) a bioreactor, (ii) an acoustic wave separator (AWS), (iii) a near infra-red (NIR) spectroscopy unit, (iv) a high-performance liquid chromatography (HPLC) unit, (v) a continuous capture chromatography, (vi) viral inactivation unit, (vii) a continuous polishing chromatography, (viii) one or more pumps, (ix) ultrafiltration-diafiltration unit, (x) in-line turbidity sensors, (xi) conductivity sensors, and (xii) a soft sensor, and wherein the soft sensor corresponds to at least one of: (a) a physics-based model, (b) a data-based model, and (c) a hybrid physics plus data-based model.

3. The processor implemented method as claimed in claim 1, further comprising, selecting, via the one or more hardware processors, at least one model for each unit operation from a model repository, wherein the at least one model corresponds to: (i) a mechanistic model, (ii) an empirical model, (iii) a rule-based model, and (iv) a data-based model, and wherein the at least one model is provided with a unique tag to activate at a same time.

4. The processor implemented method as claimed in claim 1, wherein the at least one control parameter from the model based control for at least one unit operation comprises: (a) revised set-point of control parameters, (b) profiles of control parameters for a given time period.

5. The processor implemented method as claimed in claim 1, wherein the at least one control parameter from the recipe builder at a unit operation level comprises one or more logics, and wherein one or more logics corresponds to: (i) an operating space and an operating set point for each of the unit operations, (ii) an operating set point for each of process pumps, and (iii) expected normal operating modes for each of the unit operations.

6. The processor implemented method as claimed in claim 1, wherein the at least one pre-defined control parameter in the PLC (204A) at the unit operation level comprises (i) an operating set point based on one or more standard specifications of the plurality of equipments, and (ii) prior knowledge of the plurality of equipments.

7. A system, comprising:
a memory storing instructions;
one or more communication interfaces; and
one or more hardware processors coupled to the memory via the one or more communication interfaces, wherein the one or more hardware processors are configured by the instructions to:

receive, at least input data associated with one or more equipments through a data historian, wherein the one or more equipments includes a bioreactor, an acoustic wave separator (AWS), a near infra-red (NIR) spectroscopy unit, a simulated moving bed (SMB), a high-performance liquid chromatography (HPLC) unit, wherein the at least input data corresponds to one or more process variables associated with the plurality of equipments and a data associated with at least one unit operation of protein production including an acoustic wave separation (AWS) system, a chromatography, an ultrafiltration, a depth filtration, a fermentation, separation of one or more impurities, a viral inactivation, and an ultrafiltration-diafiltration (UF-DF) unit, and wherein the one or more process variables corresponds to (i) a pressure, (ii) a turbidity, (iii) a concentration, (iv) a conductivity, (v) a pH, (vi) a temperature, and (vii) a flow rate;

generate, by a recipe builder, a sequence of unit operations to determine at least one job order created upon creating a recipe, based on the at least input data associated with the plurality of equipments for the at least one unit operation, wherein the at least one job order is transferred to a programmable logic controller (PLC) for execution via a middleware, wherein the middleware parses data received from the recipe, the middleware converts the parsed data into a PLC readable format, the middleware writes the data to the PLC, wherein the middleware maps the one or more process variables and one or more values present in the data to a PLC database and after writing the data to the PLC, the middleware communicates an acknowledgement to the recipe builder;

obtain, at least one control decision associated with at least one control parameter based on the at least one job order, wherein the at least one control decision of one or more control parameters in one or more control loops is obtained based on at least one of: (i) a model based control in which a solution of the model-based control is a single set point or multiple set points for a steady state model or one or more profiles of the one or more control parameters for a time-period for a dynamic model, or (ii) receive control parameters from the recipe builder, or (iii) using at least one pre-defined control parameter available in the PLC, or (iv) a combination thereof;

communicate, via the middleware, the at least one control decision associated with the at least one control parameter to the PLC in a PLC readable format, wherein a centralized control of an integrated continuous bioprocessing is carried out with the at least one control decision taken for a unit bioprocessing plant and/or individual equipment by integrating with the one or more control loops in a continuous bioprocessing train; and execute, by a control system of the PLC, the at least one control decision on a unit operation equipment through direct actuation with a PLC wiring, through the unit operation open platform communications (OPCs), or through automation layers over existing unit operation software interfaces to control: (i) the continuous bioprocessing train by the PLC, and (ii) an individual unit operation.

8. The system as claimed in claim 7, wherein the plurality of equipments corresponds to: (i) a bioreactor, (ii) an acoustic wave separator (AWS), (iii) a near infra-red (NIR) spectroscopy unit, (iv) a high-performance liquid chromatography (HPLC) unit, (v) continuous capture chromatography, (vi) viral inactivation unit, (vii) continuous polishing chromatography, (viii) pumps, (ix) ultrafiltration-diafiltration unit, (x) in-line turbidity sensors, (xi) conductivity sensors, and (xii) a soft sensor, and wherein the soft sensor corresponds to at least one of: (a) a physics-based model, (b) a data-based model, and (c) a hybrid physics plus data-based model.

9. The system as claimed in claim 7, wherein the one or more hardware processors are further configured by the instructions to: select, at least one model for each unit operation from a model repository, wherein the at least one model corresponds to: (i) a mechanistic model, (ii) an empirical model, (iii) a rule-based model, and (iv) a data-based model, and wherein the at least one model is provided with a unique tag to activate at a same time.

10. The system as claimed in claim 7, wherein the at least one control parameter from the model based control for at least one unit operation comprises: (a) revised set-point of control parameters, (b) profiles of control parameters for a given time period.

11. The system as claimed in claim 7, wherein the at least one control parameter from the recipe builder at a unit operation level comprises one or more logics, and wherein one or more logics corresponds to: (i) an operating space and an operating set point for each of the unit operations, (ii) an operating set point for each of process pumps, and (iii) expected normal operating modes for each of the unit operations.

12. The system as claimed in claim 7, wherein the at least one pre-defined control parameter in the PLC at the unit operation level comprises (i) an operating set point based on one or more standard specifications of the plurality of equipments, and (ii) prior knowledge of the plurality of equipments.

13. One or more non-transitory machine-readable information storage mediums comprising one or more instructions which when executed by one or more hardware processors causes:

receiving, at least input data associated with plurality of equipments through a data historian, wherein the one or more equipments includes a bioreactor, an acoustic wave separator (AWS), a near infra-red (NIR) spectroscopy unit, a simulated moving bed (SMB), a high-performance liquid chromatography (HPLC) unit, wherein the at least input data corresponds to one or more process variables associated with the plurality of equipments and a data associated with at least one unit operation of protein production including an acoustic wave separation (AWS) system, a chromatography, an ultrafiltration, a depth filtration, a fermentation, separation of one or more impurities, a viral inactivation, and an ultrafiltration-diafiltration (UF-DF) unit, and wherein the one or more process variables corresponds to (i) a pressure, (ii) a turbidity, (iii) a concentration, (iv) a conductivity, (v) a pH, (vi) a temperature, and (vii) a flow rate;

generating, by a recipe builder, a sequence of unit operations to determine at least one job order created upon creating a recipe based on the at least input data associated with the plurality of equipments for the at least one unit operation, and wherein the at least one job order is transferred to a programmable logic controller (PLC) for execution via a middleware, wherein the middleware parses data received from the recipe, the middleware converts the parsed data into a PLC readable format, the middleware writes the data to the PLC, wherein the middleware maps the one or more process variables and one or more values present in the data to a PLC database and after writing the data to the PLC, the middleware communicates an acknowledgement to the recipe builder;

obtaining, at least one control decision associated with at least one control parameter based on the at least one job order, and wherein the at least one control decision of one or more control parameters in one or more control loops is obtained based on at least one of: (i) a model based control in which a solution of the model-based control is a single set point or multiple set points for a steady state model or one or more profiles of the one or more control parameters for a time-period for a dynamic model, or (ii) receiving control parameters from the recipe builder, or (iii) using at least one pre-defined control parameter available in the PLC, or (iv) a combination thereof;

communicating, via the middleware, the at least one control decision associated with the at least one control parameter to the PLC in a PLC readable format, wherein a centralized control of an integrated continuous bioprocessing is carried out with the at least one control decision taken for a unit bioprocessing plant and/or individual equipment by integrating with the one or more control loops in a continuous bioprocessing train; and executing, by a control system of the PLC, the at least one control decision on a unit operation equipment through direct actuation with a PLC wiring, through the unit operation open platform communications (OPCs), or through automation layers over existing unit operation software interfaces to control: (i) the continuous bioprocessing train by the PLC, and (ii) an individual unit operation.

* * * * *